(12) United States Patent
Saito et al.

(10) Patent No.: US 12,201,716 B2
(45) Date of Patent: Jan. 21, 2025

(54) EXTERNAL PREPARATION FOR CONCEALING ROUGHNESS

(71) Applicant: Shiseido Company, Ltd., Tokyo (JP)

(72) Inventors: Yukari Saito, Tokyo (JP); Tomoko Ikeda, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 227 days.

(21) Appl. No.: 17/284,287

(22) PCT Filed: Oct. 10, 2019

(86) PCT No.: PCT/JP2019/039958
§ 371 (c)(1),
(2) Date: Apr. 9, 2021

(87) PCT Pub. No.: WO2020/075792
PCT Pub. Date: Apr. 16, 2020

(65) Prior Publication Data
US 2021/0330574 A1 Oct. 28, 2021

(30) Foreign Application Priority Data
Oct. 10, 2018 (JP) .................................. 2018-191972

(51) Int. Cl.
*A61K 8/92* (2006.01)
*A61Q 1/12* (2006.01)

(52) U.S. Cl.
CPC ................ *A61K 8/922* (2013.01); *A61K 8/92* (2013.01); *A61Q 1/12* (2013.01); *A61K 2800/60* (2013.01)

(58) Field of Classification Search
CPC ...... A61K 2800/10; A61K 8/25; A61K 8/891; A61K 8/895; A61K 2800/413; A61K 2800/48; A61K 2800/60; A61K 2800/654; A61K 8/0241; A61K 8/0279; A61K 8/03; A61K 8/062; A61K 8/064; A61K 8/19; A61K 8/27; A61K 8/31; A61K 8/37; A61K 8/39; A61K 8/40; A61K 8/8111; A61K 8/8147; A61K 8/8152; A61K 8/86; A61K 8/92; A61K 8/922; A61K 8/29; A61K 8/0245; A61K 2800/436; A61K 2800/43; A61K 8/06; A61K 2800/412; A61K 2800/872; A61K 8/732; A61K 8/042; A61K 2800/63; A61K 8/585; A61K 8/11; A61K 8/34; A61K 2800/28; A61K 31/715; A61K 36/889; A61K 8/022; A61K 8/025; A61K 8/361; A61K 8/73; A61K 8/9783; A61K 8/9794; A61K 9/14; A61K 2800/31; A61K 2800/621; A61K 8/044; A61K 8/20; A61K 8/60; A61K 8/64; A61K 2800/56; A61K 2800/62; A61K 2800/624; A61K 2800/651; A61K 2800/652; A61K 8/0283; A61K 8/26; A61K 8/345; A61K 8/4986; A61K 8/553; A61K 8/602; A61K 8/731; A61K 8/88; A61K 8/893; A61K 2800/33; A61K 2800/594; A61K 8/498; A61K 8/046; A61K 8/8182; A61K 8/817; A61K 8/02; A61K 2800/5426; A61K 8/736; A61K 8/8135; A61K 8/87; A61Q 1/02; A61Q 1/12; A61Q 19/00; A61Q 17/04; A61Q 1/10; A61Q 19/008; A61Q 1/06; A61Q 11/00; A61Q 15/00; A61Q 19/005; A61Q 19/007; A61Q 19/10; A61Q 5/02; A61Q 1/00; A61Q 5/12; A61Q 5/06; A61Q 9/02; A61Q 5/00

See application file for complete search history.

(56) References Cited

U.S. PATENT DOCUMENTS

| | | | |
|---|---|---|---|
| 4,536,405 A | 8/1985 | Nara et al. | |
| 4,574,082 A | 3/1986 | Tietjen et al. | |
| 9,422,315 B2 * | 8/2016 | Suenaga | A61K 8/585 556/456 |
| 2013/0315650 A1 * | 11/2013 | Cassin | A61Q 1/12 401/268 |

FOREIGN PATENT DOCUMENTS

| | | | | |
|---|---|---|---|---|
| JP | 54-037837 A | 3/1979 | | |
| JP | 60-056914 A | 4/1985 | | |
| JP | 61-018708 A | 1/1986 | | |
| JP | 04-095011 A | 3/1992 | | |
| JP | 2003520217 | * 7/2003 | ............... | A61Q 1/02 |
| JP | 2003520217 A | * 7/2003 | ............. | A61K 7/021 |
| JP | 2004203789 A | * 7/2004 | ............... | A61K 7/02 |
| JP | 2005-509610 A | 4/2005 | | |
| JP | 2005509610 | * 1/2006 | ............... | A61K 8/00 |
| JP | 2011-225563 A | 11/2011 | | |
| JP | 2012211103 A | * 11/2012 | ............... | A61Q 1/02 |

(Continued)

OTHER PUBLICATIONS

JP2003520217A translation (Year: 2003).*

(Continued)

*Primary Examiner* — Audrea B Coniglio

(74) *Attorney, Agent, or Firm* — Foley & Lardner LLP

(57) ABSTRACT

An objective of the present invention is to provide an external preparation for concealing roughness that is easy to spread when applied, while also having effects of concealing roughness such as fine wrinkles. The external preparation for concealing roughness of the present invention comprises (a) 1% to 15% by mass of a wax; and (b) 4% to 25% by mass of a non-spherical powder; and has a viscosity of 50,000 to 150,000 mPa·s.

4 Claims, No Drawings

(56) References Cited

FOREIGN PATENT DOCUMENTS

| | | |
|---|---|---|
| JP | 2014-129296 A | 7/2014 |
| TW | 200934528 A | 8/2009 |
| WO | WO-01/52795 A2 | 7/2001 |
| WO | WO-03/030857 A1 | 4/2003 |
| WO | WO-2009/098838 A1 | 8/2009 |

OTHER PUBLICATIONS

JP2012211103A translation (Year: 2012).*
JP2003520217 translation (Year: 2003).*
JP2004203789A_translation (Year: 2004).*
JP2005509610A_translation (Year: 2006).*

* cited by examiner

EXTERNAL PREPARATION FOR CONCEALING ROUGHNESS

CROSS-REFERENCE TO RELATED APPLICATIONS

This application is the U.S. National Stage of PCT/JP2019/039958, filed Oct. 10, 2019, which claims priority to JP 2018-191972, filed Oct. 10, 2018.

TECHNICAL FIELD

The present invention relates to a cosmetic for concealing roughness, which has an improved texture while providing roughness concealing effects.

BACKGROUND ART

Conventionally, cosmetics that make fine wrinkles and pores, or skin roughness such as coarseness of texture less conspicuous are desired, and various types have been considered. As such cosmetics that provide a roughness concealing effect, those that smoothen roughness on the skin and make such roughness and the like less visually conspicuous have been proposed.

Waxes are one of the raw materials that are used in such cosmetics for concealing roughness. However, although waxes have excellent roughness concealing effects, they have the problem that they tend to solidify and are difficult to spread.

For example, Patent Document 1 discloses a concealer for concealing roughness, obtained by blending a wax, a volatile oil, a non-volatile oil and a coloring pigment. With this external preparation, high roughness concealing effects are obtained by essentially blending rice bran wax into the wax, while simultaneously obtaining good applicability to skin and flexibility of the coating film by blending the volatile oil and the non-volatile oil.

However, an external preparation in which the durability and the texture of the coating film are further improved while maintaining the roughness concealing effects is desired.

RELATED ART

Patent Documents

Patent Document 1: JP 2011-162463 A

SUMMARY OF THE INVENTION

Problem to be Solved by the Invention

An objective of the present invention is to provide an external preparation for concealing roughness that is easy to spread when applied, while also having effects of concealing roughness such as fine wrinkles.

Means for Solving the Problem

As a result of performing diligent research towards solving the above-mentioned problem, the present inventors discovered that an external preparation that can be easily spread while simultaneously covering up roughness such as fine wrinkles can be obtained by blending a combination of a wax and a non-spherical powder, thereby completing the present invention.

In other words, the present invention provides an external preparation for concealing roughness, comprising (a) 1% to 15% by mass of a wax and (b) 4% to 25% by mass of a non-spherical powder, and having a viscosity of 50,000 to 150,000 mPa·s.

Effects of the Invention

Due to the above-mentioned features, the present invention can obtain an external preparation for concealing roughness, which conceals roughness of skin or the like, and which is also easy to spread even though a wax is blended therein. The external preparation of the present invention can be applied with a sufficient film thickness without degrading the feeling in use. For this reason, immediately after application, roughness such as fine wrinkles is made inconspicuous, and an application surface that is soft to the touch can be obtained.

Modes for Carrying Out the Invention

The external preparation of the present invention is characterized by comprising (a) a wax and (b) a non-spherical powder. Hereinafter, the respective ingredients constituting the external preparation of the present invention will be explained in detail.

<(a) Wax>

The (a) wax (hereinafter sometimes referred to as "component (a)") blended into the external preparation according to the present invention need only be a wax that is normally used in external preparations and is not particularly limited, as long as it is an oil-based component that is solid at ambient temperature. Specific examples include rice bran wax, candelilla wax, jojoba oil (hydrogenated jojoba oil), microcrystalline wax, paraffin wax, myristyl myristate, ceresin wax, polyethylene wax and the like.

The blended amount of component (a) should be 1% to 15% by mass, preferably 2% to 10% by mass relative to the total amount of the external preparation. If the blended amount of component (a) is less than 1% by mass, then sufficient roughness concealing effects cannot be obtained, and if more than 15% by mass is blended, then the external preparation becomes difficult to spread and the stability decreases.

<(b) Non-Spherical Powder>

The (b) non-spherical powder (hereinafter sometimes referred to simply as "component (b)") blended into the external preparation according to the present invention is a powder that is normally used in external preparations, and any type may be used without any limitations as long as it is non-spherical.

In particular, talc is preferably used in the present invention for purposes of ease of application. The talc may or may not be surface-treated. As hydrophobic surface treatment agents, those that are commonly used in the cosmetics field, for example, silicones such as dimethicone and alkyl-modified silicone, alkoxysilanes such as octyltriethoxysilane, dextrin fatty acid esters such as dextrin palmitate, fatty acids such as stearic acid, and silica or the like may be used. Although talc comes in various forms, such as flaky and lumpy, it is particularly preferable to use lumpy talc. In the present invention, talc having an average particle size of 5 to 25 μm is preferably used.

The blended amount of component (b) should be 4% to 25% by mass, preferably 5% to 10% by mass relative to the total amount of the external preparation. If the blended amount of component (b) is less than 4% by mass, then the external preparation becomes difficult to spread, and if more than 25% by mass is blended, then the external preparation becomes difficult to spread and powderiness occurs.

Furthermore, the ratio of the blended amount of the non-spherical powder relative to the wax should be 0.3 to 2.5, preferably 0.75 to 2.0.

The external preparation of the present invention has a viscosity of 50,000 to 150,000 mPa·s. The viscosity (mPa·s) mentioned here refers to the value measured by using a BH-type viscometer (Rotor No. 7, 10 rotations, 1 minute) after placing the formulated external preparation at rest for 1 day at 30° C. If the viscosity of the external preparation is less than 50,000 mPa·s, then the sense of fitting on the skin becomes worse and the external preparation is not suitable for being layered with makeup cosmetics, and if the viscosity exceeds 150,000 mPa·s, then the external preparation becomes difficult to spread and tends to become uneven.

In addition to the above-mentioned blended components, components that are generally used in compositions for external use, such as oil-soluble film-forming agents, surfactants, lower alcohols (ethanol, etc.), humectants, oils, ultraviolet absorbing agents, ultraviolet scattering agents, powders, thickeners, antioxidants, preservatives, microbicidal agents, pH adjusters, vitamins, blood flow promoters, whiteners, skin activators, medicinal components, extracts from animals or plants, colorants, fragrances and the like can be blended into the external preparation of the present invention, as needed, within a range not compromising the effects of the present invention. However, the possible components are not limited to these examples.

In particular, the roughness concealing effects and the ease of application can be further improved by blending a crosslinked siloxane elastomer into the external preparation of the present invention. Crosslinked siloxane elastomers are siloxane elastomers (silicone elastomers) obtained by three-dimensionally crosslinking polydimethylsiloxane, and are not particularly limited, including those that are emulsifying and non-emulsifying.

Emulsifying crosslinked silicone elastomers include polyoxyethylene methylpolysiloxane crosspolymers, alkyl group-containing polyoxyethylene methylpolysiloxane crosspolymers, polyglycerin-modified silicone crosspolymers, alkyl group-containing polyglycerin-modified silicone crosspolymers and the like. Non-emulsifying crosslinked silicone elastomers include methylpolysiloxane crosspolymers, methylphenylpolysiloxane crosspolymers, vinyl dimethicone/lauryl dimethicone crosspolymers, lauryl polydimethylsiloxyethyl dimethicone/bis-vinyl dimethicone crosspolymers, alkyl (C30-45) cetearyl dimethicone crosspolymers, cetearyl dimethicone crosspolymers and the like. As the crosslinked siloxane elastomers, those that are commercially available in the form of swollen matter that is swollen with various types of oils such as silicone oils, mineral oils, triethylhexanoin, squalane and the like may be used.

Commercially available products that are crosslinked siloxane elastomers that can be blended into the external preparation of the present invention include KSG-210 (mixture of ((PEG-10/15)/dimethicone) crosspolymer and dimethicone, 20% to 30% crosslinked, manufactured by Shin-etsu Chemical Co., Ltd.), KSG-360Z (mixture of (PEG-15/ lauryl polydimethylsiloxyethyl dimethicone) crosspolymer and dimethicone, 30% to 40% crosslinked, manufactured by Shin-etsu Chemical Co., Ltd.), KSG-710 (mixture of (dimethicone/polyglycerin-3) crosspolymer and dimethicone, 20% to 30% crosslinked, manufactured by Shin-etsu Chemical Co., Ltd.) and 9045 Silicone Elastomer Blend (mixture of dimethicone crosspolymer and cyclopentasiloxane, 12.6% crosslinked, manufactured by Dow Corning Toray Co., Ltd.).

When blending a crosslinked siloxane elastomer into the external preparation of the present invention, the blended amount thereof should preferably be 12% by mass or less, and preferably 0.25% to 12% by mass, in terms of solids, relative to the total amount of the external preparation. If the blended amount is too small, then the roughness concealing improvement effects cannot be sufficiently obtained, and if there is more than 12% by mass, then unevenness occurs during application and the effects tend to be reduced.

In the external preparation of the present invention, it is preferable to blend a spherical powder for improving the roughness concealing effects.

The spherical powder mentioned here refers to powders that are normally blended into external preparations in order to improve the texture, including, but not being limited to, inorganic powders such as silicic anhydride, and organic resin powders such as polymethyl methacrylate resin powders, polyamide resin powders (nylon powders), polyethylene powders, polystyrene powders, styrene and (meth) acrylic acid copolymer resin powders, benzoguanamine resin powders, polytetrafluoroethylene powders, cellulose powders and trimethyl silsequioxane powders. Commercially available products include Trefil E-506S ((dimethicone/vinyl dimethicone) crosspolymer, manufactured by Dow Corning Toray Co., Ltd.), KSP-100 ((vinyl dimethicone/methicone silsesquioxane) crosspolymer, manufactured by Shin-etsu Chemical Co., Ltd.), Nylon SP-500 (nylon-12, manufactured by Toray Industries, Inc.), Microsphere M306 (methyl methacrylate crosspolymer, manufactured by Matsumoto Yushi Seiyaku Co., Ltd.) and the like. In the present invention, a spherical powder having an average particle size of 2 to 30 μm is preferably used.

In the case in which a spherical powder is blended into the external preparation of the present invention, the blended amount thereof should be 25% by mass or less, preferably 3% to 25% by mass relative to the total amount of the external preparation. If the blended amount is too small, then the roughness concealing improvement effects cannot be sufficiently obtained, and if there is more than 25% by mass, then there is a tendency towards powderiness.

The external preparation of the present invention may be in the form of an oil, or a water-in-oil or oil-in-water emulsion such as a cream or the like. Whichever form is used, the desired skin roughness coverup effects can be obtained. In particular, the external preparation can be made more stable by providing it in the form of an oil-in-water or a water-in-oil emulsion.

Additionally, the external preparation of the present invention can be used as a base agent for various types of cosmetics, and can be formulated as a skin-care cosmetic, a sunscreen cosmetic, a makeup base, a foundation, a makeup cosmetic or the like having roughness concealing effects.

The external preparation according to the present invention does not result in powder clumping even when applied over a foundation or the like, and thus can be applied by being layered over skin to which makeup has been applied. It can also be used by being directly applied to skin to which makeup has not been applied, as one form of daily skin care.

The external preparation of the present invention can be manufactured in accordance with conventionally used methods. To explain briefly, in the case in which the external preparation of the present invention is prepared as a water-in-oil emulsion cosmetic, it can be manufactured by separately mixing the oil-based components and the water-based components while heating the components as needed, emulsifying the water phase in the oil phase, then filling a container with the resulting emulsion and gradually cooling the emulsion.

EXAMPLES

Although the present invention will be explained in further detail by providing examples below, the present invention is not limited in any way thereby. Where not otherwise noted, the blended amounts represent the percentages by mass of the components relative to the systems in which they are blended.

Before presenting the examples, the evaluation methods used in the present invention will be explained.

1. Roughness Concealing Effects

Evaluations were performed by means of actual use tests by ten expert panelists. Specifically, each sample was applied to a cheek, and the effect of making roughness such as fine wrinkles and pores on the skin after application visually inconspicuous (roughness concealing effects) was evaluated for each sample in accordance with the below-indicated evaluation criteria.

<Evaluation Criteria>
A: Eight or more panelists evaluated the results as being good
B: Five to seven panelists evaluated the results as being good
C: Three or four panelists evaluated the results as being good
D: Two or fewer panelists evaluated the results as being good 2. Ease of Application Evaluations were performed by means of actual use tests by ten expert panelists. Specifically, each sample was applied to a cheek, and the spreadability when applied was evaluated for each sample in accordance with the below-indicated evaluation criteria.

<Evaluation Criteria>
A: Eight or more panelists evaluated the results as being good.
B: Five to seven panelists evaluated the results as being good.
C: Three or four panelists evaluated the results as being good.
D: Two or fewer panelists evaluated the results as being good.

3. Stability

After formulation, the states of formulated substances after being left for two weeks at 50° C. were visually evaluated.
A: Oil/water separation was not observed and the state immediately after formulation was maintained.
B: Some oil/water separation was observed.
C: Oil/water separation was conspicuous.

Examples and Comparative Examples

1. Water-in-Oil Emulsion Cosmetic

The water-in-oil emulsion cosmetic compositions indicated in Tables 1 to 3 below were formulated. Specifically, the compositions were obtained by dispersing the powder in the oil-based components that were mixed by using a homomixer, then adding the water-based components, which were mixed until homogeneous.

TABLE 1

|  | Ex. 1 | Ex. 2 | Co. Ex. 1 | Co. Ex. 2 | Co. Ex. 3 |
|---|---|---|---|---|---|
| Cyclomethicone | 57 | 32 | 35 | 34 | 9 |
| Diphenylsiloxyphenyl trimethicone | 2 | 2 | 2 | 2 | 2 |
| Trimethylsiloxy silicic acid | 4 | 4 | 4 | 4 | 4 |
| PEG-10 dimethicone | 3 | 3 | 3 | 3 | 3 |
| Talc | 5 | 5 | 5 | 3 | 28 |
| Zinc oxide | 5 | 5 | 5 | 5 | 5 |
| Dimethicone crosspolymer 12.5%/cyclopentasiloxane | — | 25 | 25 | 25 | 25 |
| Rice bran wax | 3 | 3 | — | 3 | 3 |
| Water | 15 | 15 | 15 | 15 | 15 |
| Butylene glycol | 5 | 5 | 5 | 5 | 5 |
| (Li/Mg/Na) silicate | 1 | 1 | 1 | 1 | 1 |
| Total | 100 | 100 | 100 | 100 | 100 |
| Evaluation Roughness concealing | B | A | C | A | C |
| Ease of application | B | A | A | D | D |
| Stability | A | A | A | A | B |

As indicated in Table 1, a composition (Example 1) in which component (a) (rice bran wax) and component (b) (talc) in the present invention were blended had sufficient roughness concealing effects and spreadability. Additionally, a composition (Example 2) in which a crosslinked siloxane elastomer was blended in addition to component (a) and component (b) had further improved roughness concealing effects and ease of application in comparison with the composition of Example 1.

On the other hand, in a composition (Comparative Example 1) that did not contain component (a), although a crosslinked siloxane elastomer was blended therein, sufficient roughness concealing effects were not obtained. In a composition (Comparative Example 2) in which the blended amount of component (b) was less than 4% by mass, the spreadability was poor. In a composition (Comparative Example 3) in which the blended amount of component (b) exceeded 25% by mass, sufficient roughness concealing effects were not able to be obtained, and furthermore, the spreadability was poor.

TABLE 2

|  | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|
| Cyclomethicone | 32 | 32 | 32 | 32 | 32 | 32 | 32 | 32 | 32 | 32 |
| Diphenylsiloxyphenyl trimethicone | 2 | 2 | 2 | 2 | 2 | 2 | 2 | 2 | 2 | 2 |
| Trimethylsiloxy silicic acid | 4 | 4 | 4 | 4 | 4 | 4 | 4 | 4 | 4 | 4 |
| PEG-10 dimethicone | 3 | 3 | 3 | 3 | 3 | 3 | 3 | 3 | 3 | 3 |
| Talc | 5 | 5 | 5 | 5 | 5 | 5 | 5 | 5 | 5 | 5 |
| Zinc oxide | 5 | 5 | 5 | 5 | 5 | 5 | 5 | 5 | 5 | 5 |
| Dimethicone crosspolymer 12.5%/cyclopentasiloxane | 25 | 25 | 25 | 25 | 25 | 25 | 25 | 25 | 25 | 25 |
| Rice bran wax | 3 | — | — | — | — | — | — | — | — | — |
| Polyethylene wax | — | 3 | — | — | 1.5 | — | — | — | 1.5 |

TABLE 2-continued

|  | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|
| Microcrystalline wax | — | — | 3 | — | — | 1.5 | 1.5 | — | 1.5 | — |
| Jojoba ester | — | — | — | 3 | — | — | 1.5 | 1.5 | 1.5 | 1.5 |
| Candelilla wax | — | — | — | — | 3 | — | — | 1.5 | — | — |
| Water | 15 | 15 | 15 | 15 | 15 | 15 | 15 | 15 | 15 | 15 |
| Butylene glycol | 5 | 5 | 5 | 5 | 5 | 5 | 5 | 5 | 5 | 5 |
| (Li/Mg/Na) silicate | 1 | 1 | 1 | 1 | 1 | 1 | 1 | 1 | 1 | 1 |
| Total | 100 | 100 | 100 | 100 | 100 | 100 | 100 | 100 | 100 | 100 |
| Evaluation Roughness concealing | A | A | A | A | A | A | A | A | A | A |
| Ease of application | A | A | A | A | A | A | A | A | A | A |
| Stability | A | A | A | A | A | A | A | A | A | A |

As indicated in Table 2, with respect to the composition of Example 2, compositions (Examples 3 to 6) were formulated by changing the type of wax, and compositions (Examples 7 to 11) were formulated by changing the combination of multiple waxes that were blended. No matter which wax was used, there were sufficient roughness concealing effects, and the compositions were easy to apply and had excellent stability.

composition (Comparative Example 4) not containing component (a) and a composition (Comparative Example 5) in which the blended amount of component (a) was less than 1% by mass. With a composition (Comparative Example 6) in which the blended amount of component (a) exceeded 15% by mass, the spreadability when applied was poor and the stability was also worse. Additionally, with a composition (Comparative Example 7) in which the blended amount

TABLE 3

|  | Ex. 12 | Ex. 13 | Ex. 14 | Ex. 15 | Ex. 16 | Ex. 17 | Ex. 18 | Ex. 19 | Ex. 20 | Ex. 21 | Co. Ex. 4 | Co. Ex. 5 | Co. Ex. 6 | Co. Ex. 7 | Co. Ex. 8 | Co. Ex. 9 |
|---|---|---|---|---|---|---|---|---|---|---|---|---|---|---|---|---|
| Cyclomethicone | 32 | 32 | 32 | 32 | 32 | 32 | 32 | 32 | 32 | 32 | 35 | 34.5 | 15 | 34 | 9 | 32 |
| Diphenylsiloxyphenyl trimethicone | 2 | 2 | 2 | 2 | 2 | 2 | 2 | 2 | 2 | 2 | 2 | 2 | 2 | 2 | 2 | 2 |
| Trimethylsiloxy silicic acid | 4 | 4 | 4 | 4 | 4 | 4 | 4 | 4 | 4 | 4 | 4 | 4 | 4 | 4 | 4 | 4 |
| PEG-10 dimethicone | 3 | 3 | 3 | 3 | 3 | 3 | 3 | 3 | 3 | 3 | 3 | 3 | 3 | 3 | 3 | 3 |
| Talc | 5 | 5 | 5 | 5 | 5 | 5 | 5 | 5 | 5 | 5 | 5 | 5 | 5 | 3 | 28 | — |
| Zinc oxide | 5 | 5 | 5 | 5 | 5 | 5 | 5 | 5 | 5 | 5 | 5 | 5 | 5 | 5 | 5 | 10 |
| Dimethicone crosspolymer 12.5%/cyclopentasiloxane | 20 | 20 | 20 | 20 | 20 | 20 | 20 | 20 | 20 | 20 | 20 | 20 | 20 | 20 | 20 | 20 |
| (Dimethicone/vinyl dimethicone) crosspolymer (spherical powder) | 5 | 5 | 5 | 5 | 5 | 5 | 5 | 5 | 5 | 5 | 5 | 5 | 5 | 5 | 5 | 5 |
| Rice bran wax | 3 | — | — | — | — | — | — | — | — | — | — | 0.5 | 20 | 3 | 3 | 3 |
| Polyethylene wax | — | 3 | — | — | — | 1.5 | — | — | 1.5 | 1.5 | — | — | — | — | — | — |
| Microcrystalline wax | — | — | 3 | — | — | 1.5 | 1.5 | — | — | — | — | — | — | — | — | — |
| Jojoba ester | — | — | — | 3 | — | — | 1.5 | 1.5 | 1.5 | — | — | — | — | — | — | — |
| Candelilla wax | — | — | — | — | 3 | — | — | 1.5 | — | 1.5 | — | — | — | — | — | — |
| Water | 15 | 15 | 15 | 15 | 15 | 15 | 15 | 15 | 15 | 15 | 15 | 15 | 15 | 15 | 15 | 15 |
| Butylene glycol | 5 | 5 | 5 | 5 | 5 | 5 | 5 | 5 | 5 | 5 | 5 | 5 | 5 | 5 | 5 | 5 |
| (Li/Mg/Na) silicate | 1 | 1 | 1 | 1 | 1 | — | — | — | — | — | 1 | 1 | 1 | 1 | 1 | 1 |
| Total | 100 | 100 | 100 | 100 | 100 | 100 | 100 | 100 | 100 | 100 | 100 | 100 | 100 | 100 | 100 | 100 |
| Evaluation Roughness concealing | A | A | A | A | A | A | A | A | A | A | C | C | B | B | C | D |
| Ease of application | A | A | A | A | A | A | A | A | A | A | B | B | D | D | D | B |
| Stability | A | A | A | A | A | A | A | A | A | A | A | A | C | A | B | A |

In Table 3, a composition (Example 12) was formulated by further blending a crosslinked siloxane elastomer and a spherical powder in addition to component (a) and component (b) of the present invention. With respect to the composition of Example 12, compositions (Examples 13 to 16) were formulated by changing the type of wax, and compositions (Examples 17 to 21) were formulated by changing the combination of multiple waxes that were blended. For each composition, there were sufficient roughness concealing effects, and the compositions were easy to apply and had excellent stability.

On the other hand, even if a crosslinked siloxane elastomer and a spherical powder were blended, sufficient roughness concealing effects were not able to be obtained with a composition (Comparative Example 4) not containing component (a) and a composition (Comparative Example 5) in which the blended amount of component (a) was less than 1% by mass. With a composition (Comparative Example 6) in which the blended amount of component (a) exceeded 15% by mass, the spreadability when applied was poor and the stability was also worse. Additionally, with a composition (Comparative Example 7) in which the blended amount of component (b) was less than 4% by mass, the spreadability was poor, and with a composition (Comparative Example 8) in which the blended amount of component (b) was more than 25% by mass, sufficient roughness concealing effects were not able to be obtained, and furthermore, the spreadability became poor. Additionally, sufficient roughness concealing effects were not able to be obtained even when raising the blended amount of zinc oxide, which has light scattering effects, instead of component (b) (Comparative Example 9).

2. Oil-Based Cosmetic

The oil-based cosmetic compositions indicated in Table 4 below were formulated. Specifically, the compositions were obtained by dispersing the powder in the oil-based components that were mixed by using a homomixer.

TABLE 4

|  | Ex. 22 | Ex. 23 | Ex. 24 | Ex. 25 | Ex. 26 | Ex. 27 | Ex. 28 | Ex. 29 |
| --- | --- | --- | --- | --- | --- | --- | --- | --- |
| Cyclomethicone | 53 | 53 | 53 | 53 | 53 | 53 | 53 | 53 |
| Diphenylsiloxyphenyl trimethicone | 2 | 2 | 2 | 2 | 2 | 2 | 2 | 2 |
| Trimethylsiloxy silicic acid | 4 | 4 | 4 | 4 | 4 | 4 | 4 | 4 |
| PEG-10 dimethicone | 3 | 3 | 3 | 3 | 3 | 3 | 3 | 3 |
| Talc | 5 | 5 | 5 | 5 | 5 | 5 | 5 | 5 |
| Zinc oxide | 5 | 5 | 5 | 5 | 5 | 5 | 5 | 5 |
| Dimethicone crosspolymer 12.5%/cyclopentasiloxane | 20 | 20 | 20 | 20 | 20 | 20 | 20 | 20 |
| (Dimethicone/vinyl dimethicone) crosspolymer (spherical powder) | 5 | 5 | 5 | 5 | 5 | 5 | 5 | 5 |
| Rice bran wax | 3 | — | — | — | — | — | — | — |
| Polyethylene wax | — | 3 | — | — | — | 1.5 | — | 1.5 |
| Microcrystalline wax | — | — | 3 | — | — | 1.5 | 1.5 | — |
| Jojoba ester | — | — | — | 3 | — | — | 1.5 | 1.5 |
| Candelilla wax | — | — | — | — | 3 | — | — | — |
| Total | 100 | 100 | 100 | 100 | 100 | 100 | 100 | 100 |
| Evaluation Roughness concealing | A | A | A | A | A | A | A | A |
| Ease of application | B | B | B | B | B | B | B | B |
| Stability | A | A | A | A | A | A | A | A |

As indicated in Table 4, an oil-based cosmetic composition (Example 22) in which component (a) and component (b) of the present invention were blended was formulated. Furthermore, with respect to the composition of Example 22, compositions (Examples 23 to 26) were formulated by changing the type of wax, and compositions (Examples 27 to 29) were formulated by changing the combination of multiple waxes that were blended. Each of the oil-based compositions obtained sufficient roughness concealing effects and ease of application, and had excellent stability, though they were less easy to apply in comparison with the water-in-oil emulsion compositions.

The invention claimed is:

1. An external preparation for concealing roughness, comprising:
    (a) 1% to 10% by mass of a wax;
    (b) 4% to 25% by mass of a non-spherical powder having an average particle size of 5 μm to 25 μm; and
    (d) 3% to 25% by mass of a spherical powder having an average particle size of 2 μm to 30 μm; and
    having a viscosity of 50,000 to 150,000 mPa·s,
    wherein the (b) non-spherical powder is not coupled to the (d) spherical powder and
    wherein the (d) spherical powder is one or more selected from silicic anhydride, polymethyl methacrylate resin powders, polyethylene powders, polystyrene powders, styrene and (meth) acrylic acid copolymer resin powders, benzoguanamine resin powders, polytetrafluoroethylene powders, cellulose powders, trimethyl silsesquioxane powders, (dimethicone/vinyl dimethicone) crosspolymer and (vinyl dimethicone/methicone silsesquioxane) crosspolymer.

2. The external preparation as in claim 1, wherein a ratio of the (b) non-spherical powder to the (a) wax is 0.3 to 2.5.

3. The external preparation as in claim 1, further comprising (c) a crosslinked siloxane elastomer.

4. The external preparation as in claim 1, which is a water-in-oil emulsion cosmetic or an oil-based cosmetic.

* * * * *